(12) United States Patent
Jais et al.

(10) Patent No.: US 12,702,322 B2
(45) **Date of Patent: *Aug. 11, 2026**

(54) DEVICES, SYSTEMS, AND METHODS FOR IMPROVING THE ACCURACY AND UTILITY OF IMAGING FOR CARDIOVASCULAR PROCEDURES

(71) Applicant: CLPH, LLC, West Valley City, UT (US)

(72) Inventors: Pierre Jais, Bordeaux (FR); Remi Dubois, Merignac (FR); Stephen Arie Leeflang, Sandy, UT (US); Christian Scott Eversull, Palo Alto, CA (US)

(73) Assignee: CLPH, LLC, West Valley City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/587,848

(22) Filed: Feb. 26, 2024

(65) Prior Publication Data

US 2024/0277251 A1 Aug. 22, 2024

Related U.S. Application Data

(63) Continuation of application No. 16/435,270, filed on Jun. 7, 2019, now Pat. No. 11,911,143.

(60) Provisional application No. 62/681,813, filed on Jun. 7, 2018.

(51) Int. Cl.
*A61B 5/06* (2006.01)
*A61B 5/00* (2006.01)

(52) U.S. Cl.
CPC ............ *A61B 5/066* (2013.01); *A61B 5/0044* (2013.01); *A61B 5/7425* (2013.01)

(58) Field of Classification Search
CPC ........... A61B 2017/00243; A61B 2017/00053; A61B 2017/00694; A61B 2034/2051; A61B 2090/374; A61B 5/0044; A61B 5/062; A61B 5/066; A61B 5/6852; A61B 5/7425

See application file for complete search history.

(56) References Cited

U.S. PATENT DOCUMENTS

2002/0045809 A1* 4/2002 Ben-Haim ........ A61M 25/0133 607/9
2008/0021336 A1* 1/2008 Dobak, III ........... A61B 5/1102 600/508
2018/0132938 A1* 5/2018 Everling ............. A61B 5/0044

* cited by examiner

*Primary Examiner* — Amelie R Davis
(74) *Attorney, Agent, or Firm* — William A. English; Vista IP Law Group LLP

(57) ABSTRACT

Apparatus and methods are provided for using catheters to increase the accuracy of anatomical maps in the setting of patient movement.

20 Claims, 3 Drawing Sheets

140A
134A
114A
142A
120A
108A
130A
117A
122A
132A 116A
110A
112A
116A
136A
140B(1)
134B
108B
130B
122B
110B
114B
132B
140B(2)

117B
116B
136B
140C(1)
134C
108C
130C
120C
114C
110C
132C

140C(2)
117C
112C
116C
136C
114D
134D
140D
120D
142D
108D
130D
117D
122D
132D 116D
110D
112D
116D
136D

DEVICES, SYSTEMS, AND METHODS FOR IMPROVING THE ACCURACY AND UTILITY OF IMAGING FOR CARDIOVASCULAR PROCEDURES

RELATED APPLICATION DATA

The present application is a continuation of co-pending U.S. application Ser. No. 16/435,270, filed Jun. 7, 2019, and issuing as U.S. Pat. No. 11,911,143, which claims benefit of U.S. provisional application Ser. No. 62/681,813, filed Jun. 7, 2018, the entire disclosures of which are expressly incorporated by reference herein.

FIELD OF THE INVENTION

The present invention relates generally to systems and methods for improving imaging during medical procedures, e.g., cardiovascular procedures, and to apparatus and methods for making and using catheters including positional sensors for imaging systems for such procedures. More particularly, the invention relates to catheter devices including positional sensors to improve the accuracy of electro-anatomical maps of the heart and to systems and methods for using such devices.

BACKGROUND

Electro-anatomical mapping has become a common adjunct to interventional cardiology procedures. In particular, this technique is used in the electrophysiology suite to enable accurate placement of catheters in the heart, e.g., for performing ablation procedures. A three-dimensional representation of the heart, including the endocardial surface can be created by introducing a catheter into the heart that includes one or more positional sensors and/or one or more sensors capable of identifying contact or proximity to anatomical structures, e.g., the endocardial surface.

Commonly, an external electromagnetic field generator is placed near the patient such that the generated field encompasses an area of interest, e.g., within the patient. A catheter including an antenna or sensor capable of interacting with the generated field is then introduced into the patient, e.g., into the patient's heart. As is generally known in the art and is available in multiple commercial imaging systems, such antennae and/or sensors can then be located or tracked with a high level of accuracy in three-dimensional space. As the catheter comes into contact with or its proximity to certain anatomical structures can be otherwise determined, one or more points in three-dimensional space can be registered and multiple such points can be combined to create a spatial representation of the patient's anatomy, e.g., the patient's heart. Such spatial maps may be overlaid or co-registered with other imaging modalities, such as MRI, CT, ultrasound imaging, impedance maps, and/or maps of electrical activity. As such, highly functional and intuitive anatomical representations, e.g., of the heart, can be constructed and used to guide interventional procedures in real time.

However, where such maps are constructed with respect to an external frame of reference, e.g., an electro-magnetic field created external to the patient, the created map may be subject to significant inaccuracy in certain common circumstances, for example, when a patient moves with respect to the externally generated frame of reference and/or wherein there are changes in certain physiologic parameters, such as changes in lung volume, respiratory cycle, volume status, and the like.

Accordingly, it would be useful to have devices and methods that correct the spatial relationship between a previously created map and an external frame of reference in order to accurately represent the anatomy after patient movement or physiologic changes.

SUMMARY

The present invention is directed to systems and methods for imaging during medical procedures, such as cardiovascular procedures, and to apparatus and methods for making and using catheters including positional sensors for imaging systems for such procedures. More particularly, the invention is directed to catheter devices incorporating positional sensors to improve the accuracy of electro-anatomical maps of the heart, and to systems and methods for using such devices.

In accordance with an exemplary embodiment, a system is provided for facilitating imaging a patient during a medical procedure that includes an electromagnetic field generator for generating an electromagnetic field around a desired region of a patient's body to provide an external reference frame; an elongate member comprising a proximal end, a distal end sized for introduction into the patient's body, and a distal portion carrying a plurality of sensors spaced apart from one another such that the sensors may be positioned within the patient's body; and a processor coupled to the sensors for receiving signals from the sensors generated in response to the electromagnetic field, the processor configured to identify when the plurality of sensors move relative to the external reference frame to identify corresponding movement of the patient's body.

In accordance with another embodiment, a method is provided for maintaining a stable spatial reference frame relative to cardiac anatomy within a patient's heart that includes introducing a distal portion of an elongate member into the patient' heart such that a first sensor carried on the distal portion is positioned within a coronary sinus and a second sensor is positioned within a tributary vein; generating an electromagnetic field that encompasses the patient's heart to provide an external reference frame; receiving signals from the first and second sensors to identify locations of the first and second sensors relative to the external reference frame; identifying when the locations of the first and second sensors move relative to the external reference frame to identify movement of the patient's heart; and compensating for movement of the patient's heart in images presented on a display.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
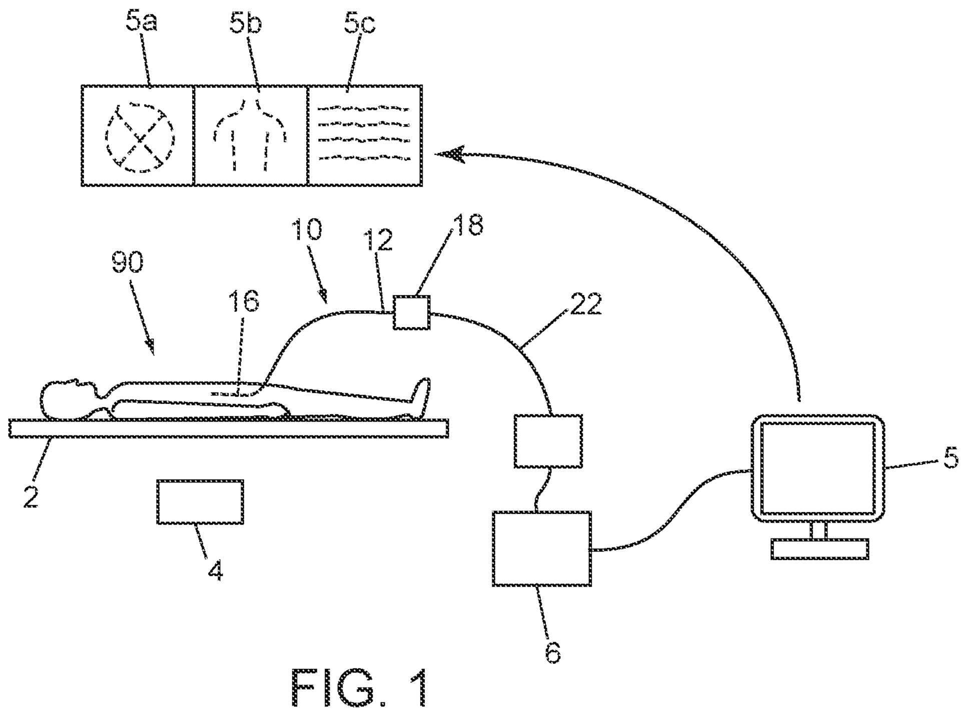
FIG. 1 is a schematic showing an exemplary arrangement of equipment in a catheterization laboratory for performing a medical procedure with a patient on a procedural table.
Figure 2:
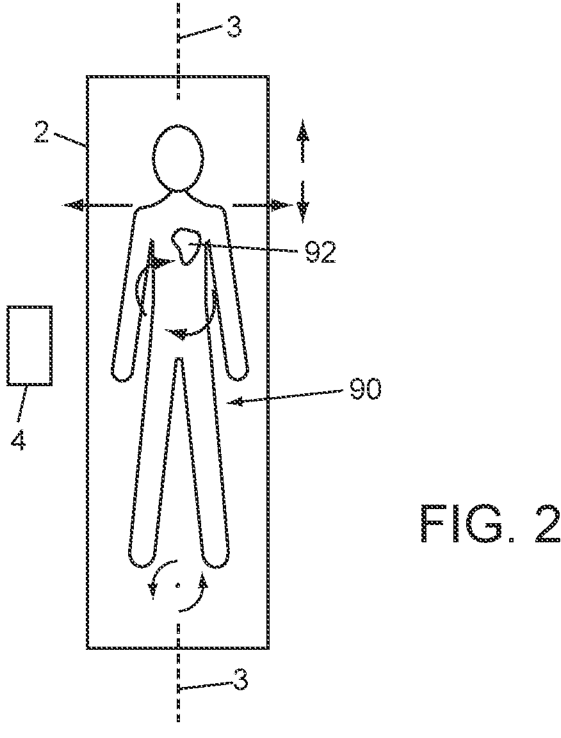
FIG. 2 depicts a typical patient position and possible patient movement on the procedural table shown in FIG. 1.

Turning to the drawings, FIGS. 1 and 2 show an exemplary arrangement of equipment that may be provided in a catheterization laboratory or other setting that may include a system 1 to facilitate imaging and/or otherwise performing a medical procedure within a patient's body 90, e.g., while the patient 90 is lying on a procedural table 2. Generally, the system 1 includes a field generator 4 mounted to or provided adjacent the table 2, e.g., positioned and/or oriented to generate an electromagnetic field encompassing an anatomical region of interest, e.g., including a patient's heart 92. As described further elsewhere herein, the electromagnetic field may provide an external reference frame that remains substantially stationary relative to the table 2 and within which one or more devices, e.g., catheter 10 shown in FIG. 1, may be identified and located, to facilitate locating and/or manipulating devices within the patient's body 90.

The system 1 may include a processor or controller 6 that communicates with the field generator 4 and/or devices (e.g., catheter 10) introduced into the patient's body, e.g., to identify the location of one or more sensors on the devices relative to the external reference frame to facilitate a physician performing a procedure. The processor 6 may also communicate with one or more displays 5 of the system 1, which may be present information to the physician to facilitate locating and/or manipulating devices within the patient's body and/or otherwise performing the procedure.

For example, as shown in FIG. 1, a previously created electro-anatomical map may be displayed on screen 5*a*. Such maps and systems for their creation are commercially available, e.g., the Carto® system from Biosense Webster, Inc., the EnSite™ Navx™ system from St. Jude Medical, or the Rhythmia HDx™ mapping system from Boston Scientific, Inc. Such systems generally include a catheter (not shown), carrying an antenna or sensor capable of interacting with the generated field, that is introduced into the patient's body. For example, the processor 6 (or another dedicated processor of the mapping system) may locate or track the antenna or sensor with a high level of accuracy in three-dimensional space relative to the external reference frame. As the catheter contacts or comes within proximity of anatomical structures, the processor may register one or more points in three dimensional space relative to the external reference frame, and combine multiple such points to create a spatial representation of the anatomy, e.g., of the patient's heart 92, which may be presented on screen 5*a*. Such spatial maps may be overlaid or co-registered with other imaging modalities, such as MRI, CT, ultrasound imaging, impedance maps, and/or maps of electrical activity, to provide visual information to the physician.

Simultaneously, one or more screens on the display(s) 5 may present additional information during the procedure. For example, screen 5*b* shows a fluoroscopic image, which may be used to navigate devices and/or image the patient's anatomy, and screen 5*c* may include a series of electrograms or other patient information, e.g., as are commonly generated during an electrophysiology procedure.

FIG. 2 shows a patient 90 positioned on a procedural table 2, illustrating certain types of typical movement of the patient's body, e.g., with up/down movement and roll movement being relatively less constrained than side/side or twist movements. For example, a patient may move side-to-side and up-or-down relative to the table 2, or may twist or rotate within the plane of the table 2. In addition, the patient's body may move up away from the table 2, e.g., in response to a cardioversion. Such movements may change the patient's anatomy relative to the external reference frame of the generated field of the field generator 4.

Thus, although the external reference frame provided by the field generator 4 may remain stationary relative to the table 2, the patient 90 may move relative to the table 2 during a procedure even if partially constrained. In addition, internal anatomy of the patient 90 may move or change in response to certain physiologic changes, e.g., the heart 92 may change shape or position, e.g., due to its expansion/contraction, patient volume status change, lung volume changes, and the like.

To provide stable spatial reference with respect to an anatomical structure or structures of interest, e.g. the heart 92, and/or to provide a dynamic spatial reference that changes in a predictable manner when certain physiologic changes occur, the system 1 includes a catheter 10, which may be introduced into the patient's body 90, e.g., into the patient's heart 92. Generally, as described further below, the catheter 10 includes a plurality of sensors whose location may be identified by the processor 6 to identify when the patient's heart 92 and/or body 90 move relative to the reference frame. Based on the identified movement, the processor 6 may modify the information presented on the display(s) 5 and/or provide other compensation relative to the external reference frame, e.g., to provide the physician a dynamic spatial reference while performing the procedure, which may allow the physician to continue manipulating devices and/or accurately performing the procedure at desired anatomical locations despite the movement.

Figures 3, 3A:
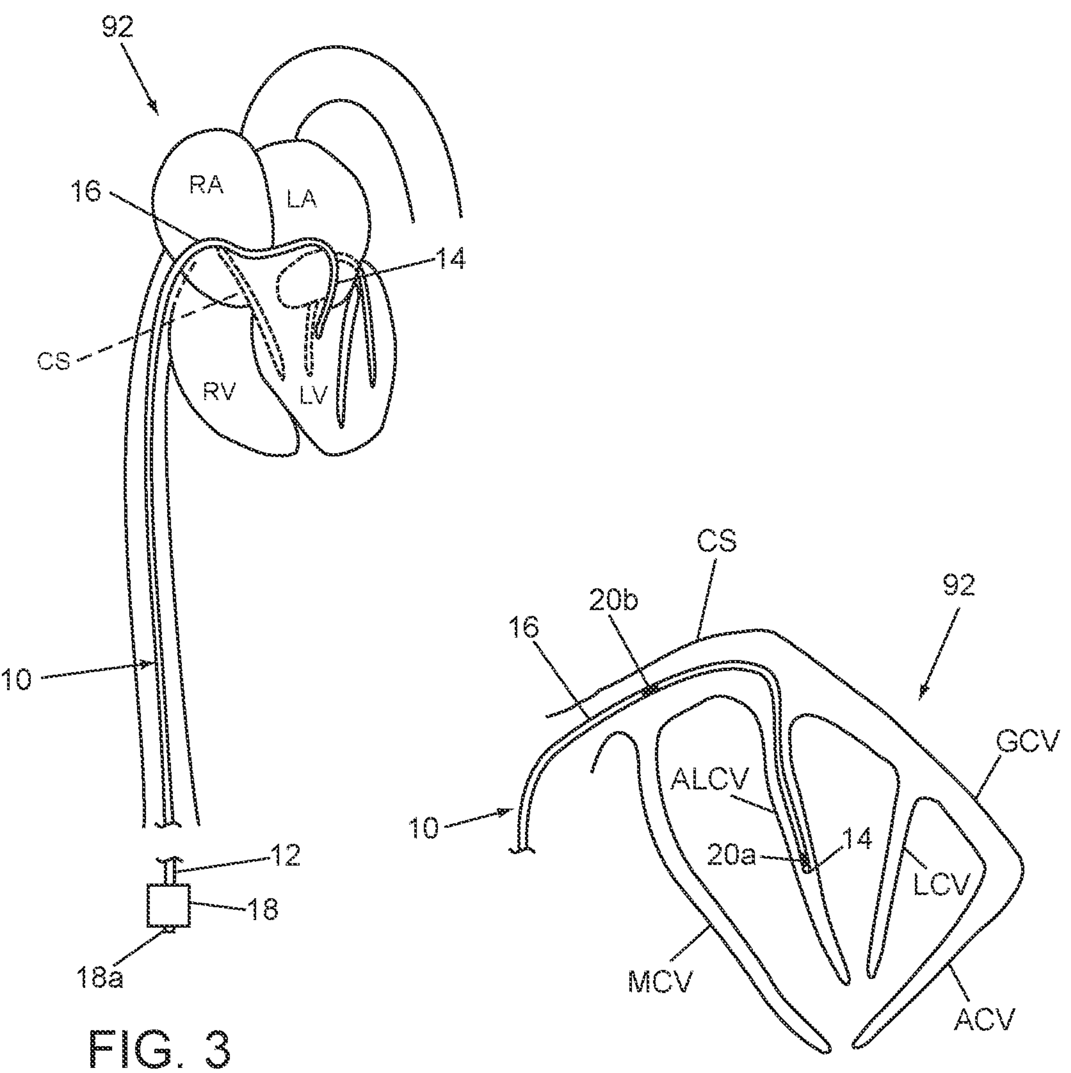
FIG. 3 is a cross-sectional view of a patient's body showing an exemplary embodiment of a catheter including a plurality of positional sensors positioned within a coronary sinus and a tributary vein of the patient's heart.
FIG. 3A is a detail showing a distal portion of the catheter of FIG. 1 showing sensors positioned within a coronary sinus and a tributary vein of the patient's heart.

Turning to FIG. 3, an example of a catheter 10 is shown that has been introduced into the patient's heart 92, e.g., positioned in the coronary sinus CS and/or great cardiac vein or a tributary thereto, e.g., the anterior lateral cardiac vein ALCV, of the heart 92, as shown in FIG. 3A. Generally, the catheter 10 is an elongate tubular member including a proximal end 12, a distal end 14 sized for introduction into the patient's body, e.g., into the patient's vasculature from a peripheral location, and a distal portion 16 carrying a plurality of antennae or sensors 20 that are coupled to the processor 6, e.g., via one or more leads (not shown) extending between the distal portion 16 and the proximal end 12. The catheter 10 may include a handle or hub 18 on the proximal end 12, e.g., including one or more actuators, connectors, and the like. For example, a connector 18*a* may be provided on the hub 18 such that a cable 22 may be coupled between the lead(s) of the sensors 20 and the processor 6 such that the processor 6 may receive signals from the sensors 20.

In an exemplary embodiment, the distal portion 16 may be flexible and/or deflectable, an intermediate portion may be flexible or semi-rigid, and a proximal portion, e.g., adjacent the proximal end 12, may be rigid or semi-rigid, e.g., to facilitate advancement of the distal portion 16 within the patient's body 90 from the proximal end 12 outside the patient's body 90. Optionally, the distal portion 16 may be steerable, e.g., may include one or more steering elements that control bending or otherwise directing the distal portion 16 from a generally straight or relaxed configuration to a curved or curvilinear configuration, for example, to facilitate manipulation of the distal portion 16 within a patient's body, e.g., to direct the distal end 14 into the coronary sinus CS from the right atrium RA of the heart 92. In this option, the catheter 10 may include one or more actuators, e.g., one or more sliders or dials (not shown) on the hub 18, that may be manipulated to bend or otherwise direct the distal portion 16 to facilitate introducing the distal end 14 into desired passages within the patient's vasculature.

In addition or alternatively, the catheter 10 may include one or more lumens (not shown) extending between the proximal and distal ends 12, 14, e.g., a guidewire lumen to allow a guidewire or other rail (also not shown) to be backloaded into the catheter 10 or otherwise facilitate introduction of the distal end 14 of the catheter 10 into the patient's body and/or desired body lumens over a guidewire.

In the example shown in FIGS. 3 and 3A, the catheter 10 includes at least a first antennae or sensors 20*a*, 20*b* spaced apart on the distal portion 16, e.g., a first sensor 20*a* adjacent the distal end 14 and a second sensor 20*b* spaced apart a predetermined minimal distance proximal to the first sensor 20*a*. Examples of such sensors that may be used in conjunction with a field generator and systems to render positional information are produced, for example, by Northern Digital, Inc.

In an exemplary embodiment, at least one of the sensors 20 may be a six degree of freedom (6DOF) sensor, i.e., providing signals corresponding to a coordinate position of the sensor in three-dimensional space within the reference frame (e.g., x-y-z), and a rotational position (e.g., pitch-yaw,-roll) of the sensor relative to the external reference frame to identify a location and orientation of the sensor, and the other sensor may provide signals corresponding only to location in three-dimensional space (e.g., x-y-z). In this example, the processor 6 may analyze the signals to identify a plane or other geometric form defined by the sensors relative to the external reference frame to provide an internal reference frame that may be substantially fixed relative to one or more regions of the patient's heart, e.g., to identify the orientation of the coronary sinus CS and/or cardiac veins. Alternatively, two sensors providing only three dimensional positional coordinates (3DOF) may define a line between them to provide a two-dimensional internal reference frame. In a further alternative, three or more 3DOF sensors may be provided on the distal portion that provide signals identifying positional coordinates of the sensors, which the processor 6 may analyze to identify a plane or other geometric form indicative of the location and/or orientation of a region of the patient's heart. Further, any number of additional sensors capable of location within a predetermined number of degrees of freedom may be provided on the catheter, which may enhance the accuracy of the resulting internal reference frame, limited only by cost and complexity of construction of the catheter.

The processor 6 may map or otherwise synchronize the resulting internal reference frame relative to the external reference frame such that, subsequent movement that results in the internal reference frame moving relative to the external reference frame may be used to reestablish the position and/or orientation of the patient's anatomy relative to the external reference frame. For example, the processor 6 may synchronize the internal reference frame with anatomical or spatial maps or other information regarding the patient's anatomy, e.g., to provide a stable spatial reference with respect to one or more anatomical structures of interest, e.g., the heart, and/or to provide a dynamic spatial reference that changes in a predictable manner when certain physiologic changes occur.

For example, when a spatial map has been previously created (and is presented on a display 5) and the patient and/or an anatomical structure moves relative to the external reference frame, the sensors 20 may provide a predictably stable or predictably dynamic reference to the anatomy. For example, when the processor 6 identifies that the sensors 20, and consequently the patient's heart or other anatomy, has moved relative to the external reference frame, the processor 6 may determine the new orientation of the internal reference frame relative to the external reference frame and compensate the spatial map accordingly.

The processor 6 may analyze any changes in position (or orientation) over time of the sensors 20 (and resulting internal reference frame) to define offsets with respect to the external reference frame of the generated field, e.g., between an originally created anatomical map to provide a revised map that accurately depicts the anatomical position after movement. Accordingly, with the distal portion 16 and sensors 20 of the catheter 10 placed within the patient's body, the sensors 20 remain stable or predictably positioned with respect to the anatomy even during movement. It will be appreciated that the sensors 20 may also be located accurately within the generated field at any point in time. Thus, the catheter 10 and sensors 20 may be used to define the relationship of the anatomy to the external reference frame even during movement of the anatomy within the generated field.

In an exemplary method, the distal end 14 of the catheter 10 may be introduced into the patient's vasculature at a peripheral location, e.g., from a puncture site at the patient's femoral, axillary, or other suitable vein, and advanced into the patient's heart 92, e.g., into the right atrium RA. The distal end 14 may be manipulated within the right atrium RA to access the coronary sinus CS, and the distal end 14 may be advanced to position the distal end 14 and first sensor 20*a* within a cardiac vein, e.g., the anterior lateral cardiac vein ALCV, with the second sensor 20*b* remaining within the coronary sinus CS, as shown in FIG. 3A. For example, the length of the distal portion 16 and/or the distance between the sensors 20 may allow the sensors 20 to be as widely separated as possible while both being positioned stably with respect to the cardiac anatomy and delivered by a single catheter or single catheter system. For example, the diameter or other cross-section of the distal portion 16 may be such that the distal portion 16 may be placed within the coronary sinus CS and/or tributary veins with minimal lateral movement, e.g., such that the location of the sensors 20 may accurately reflect the location of the coronary sinus CS and/or tributary veins. The processor 6 may then use this stable position to generate the internal reference frame, which may be used to identify movement of the patient's body 90 and/or heart 92 relative to the external reference frame.

The sensors 20*a*, 20*b* may be fixedly positioned on the catheter 10, e.g. with a separation distance of between about five and fifteen centimeters (5-15 cm). Alternatively, one or more sensors may be slidably disposed relative to the catheter body such that the distance between the sensors may be adjusted in a desired manner, e.g., as shown in the embodiments shown in FIGS. 4A-4D and described further elsewhere herein. For example, in this alternative, during use, the first or distal sensor may be advanced through the coronary sinus CS into a desired tributary vein (e.g., into the ALCV, as shown in FIG. 3A), after which the location of the second or proximal sensor may be adjusted, e.g. to maximize the separation between sensors while maintaining both in stable anatomical positions with respect to the anatomy of interest, e.g., relative to the heart.

Optionally, the catheter 10 may be constructed in order to constrain or substantially constrain certain aspects of the positional relation between two or more sensors, e.g., the sensors 20*a* and 20*b*. In addition to determining or substantially determining a path distance between sensors, the catheter may be constructed to constrain or substantially constrain independent rotation of the sensors around the axis of the catheter, e.g., the catheter segment joining the sensors may be substantially resistant to torque. Likewise, the catheter segment between the sensors may be may be constructed to bend or substantially bend in a single plane. Accordingly, the constraints on relative sensor motion imparted by the catheter may be used to more accurately define a plane or other geometric form indicative of the location and/or orientation of a region of the patient's anatomy, e.g., the patient's heart. Alternatively, such mechanical constraints on the relative position of the sensors may enable the use of less capable sensors to achieve equivalent spatial determination.

The tributary vein for the distal sensor may be selected in order to increase the fidelity, accuracy, and/or stability of the spatial relationship of the sensor array relative to the anatomy of interest. For example, as shown in FIG. 3A, in the case of ventricular ablation, the distal most sensor 20*a* may be positioned in a cardiac vein, e.g., the anterior lateral cardiac vein ALCV, adjacent an ablation target in the left ventricle LV such that this anatomical region is most stable relative to the position of the distal sensor 20*a*. As a further example, the distal portion 16 of the catheter 10 may be positioned within the patient's heart 90 such that a straight line between the sensors 20*a*, 20*b* does not extend substantially parallel to a longitudinal axis 3 (e.g., as shown in FIG. 2), e.g., defining an angle relative to the axis 3 of at least about forty five degrees (45°). In this way, sensors that provide signals corresponding only to their location (e.g., identifying their x-y-z position within the external reference frame and not capable of accurately reporting their full six degree of freedom position) may be used to provide a substantially stable internal reference frame in the setting of most common patient movement, e.g. up/down and roll (as depicted in FIG. 2).

Alternatively, each of the sensors 20*a*, 20*b* may be capable of providing signals reporting their position accurately with six degrees of freedom. In this case, two sensors may improve the accurate correlation to the anatomy by defining multiple stable points on the patient's anatomy. For example, a distal portion of a catheter carrying two 6DOF sensors placed only in the coronary sinus may be subject to small movements, e.g., if the distal portion 16 is smaller than the coronary sinus CS, which typically has a diameter being between about ten and twelve millimeters (10-12 mm) in diameter or up to about fifteen millimeters (15 mm). If the distal sensor 20*a* is advanced further into a tributary vein, e.g., the ALCV, that approximates the diameter of the distal portion 16 of the catheter 10, the sensor 20*a* may be more fully constrained in its position relative to the anatomy. Moreover, the anatomical position may be determined as a composite of or based on the position of both sensors' positions. Optionally, the catheter 10 may include features to stabilize its position within a chamber or vessels that this larger than the catheter. If in a vessel, this may include, for example a balloon, molly bolt feature, and/or other radial extension that contact the vessel wall. In a chamber, this may include a pre-shape, and/or an anchor or other such stabilizing feature.

Optionally, the positions of the sensors may be further identified relative to the external reference frame, e.g., during introduction, similar to the methods used to generate spatial maps of the heart. For example, the course of the patient's coronary venous system may be defined during introduction of the distal portion 16 of the catheter 10, e.g., through the right atrium RA into the coronary sinus CS and/or the coronary veins. The coronary vein path identified by obtaining points during advancement of the sensors 20 may then be overlaid on or co-registered with pre-existing imaging, e.g. CT scan, MRI, etc. to define a more comprehensive model of the heart anatomy. This model may then be mapped to the internal reference frame provided by the sensors 20 to subsequently compensate for positional changes of the anatomy with respect to the external reference frame.

Optionally, to further increase the accuracy of compensation, e.g., following observed patient movement, a mapping catheter or other catheter, used in conjunction with an electro-anatomical mapping system, may be positioned in a known anatomical location, e.g., in a pulmonary vein, left anterior artery (LAA), at a pre-existing transeptal puncture, and the like, and the spatial information from the three or more sensors may be used independently or be combined to reestablish the correct relationship of the anatomy (and internal reference frame) to the exterior reference frame.

Turning to FIGS. 4A-4D, examples of catheter devices are shown that include sensors whose relative location and/or spacing can be adjusted. Generally, the devices 108 include a main or outer catheter body 110 including a proximal end 112, a distal end 114 sized for introduction into a patient's body, and, optionally, one or more sensors 120, and a secondary or inner catheter body 130 also including a proximal end 132, a distal end 134 sized for introduction into a patient's body, and, optionally, one or more sensors 140. One or more catheter incorporating antennae and/or sensors and/or electrodes as shown herein may be used independently or in combinations. In the embodiments depicted, the main and secondary catheter bodies 110, 130 may be slidably disposed with respect to each other, e.g., such that the distal end 134 of the secondary catheter body 130 may be advanced and/or retracted relative to the main catheter body 110, e.g., to adjust spacing of the sensors 130, 140.

One or both of the main and secondary catheter bodies 110, 130 may include a hub or handle 116, 136, which may include one or more valves, connectors, and/or other features (not shown) in order to facilitate introduction into the body, maintenance of hemostasis, connection to a system for receiving/transmitting signals/energy to/from the sensors and/or electrodes. For example, each of the bodies 110, 130 may include one or more leads extending from the sensors 120, 140 to corresponding connectors (not shown) on the hubs 116, 136 to facilitate coupling the sensors 120, 140 to a processor or controller (not shown). The catheter construction may optimize torque, shape, flexibility, and/or other mechanical features to enable reliable and expeditious placement in the coronary veins. For example, in the embodiments shown in FIGS. 4A and 4D, a distal portion 116A, 116D of the main catheter body 110A, 110D may include a pre-shaped distal segment, e.g., biased to a predetermined curved or curvilinear shape, which may facilitate cannulating a coronary sinus when introduced into a right atrium of a heart (not shown).

Figures 4A, 4B, 4C, 4D:
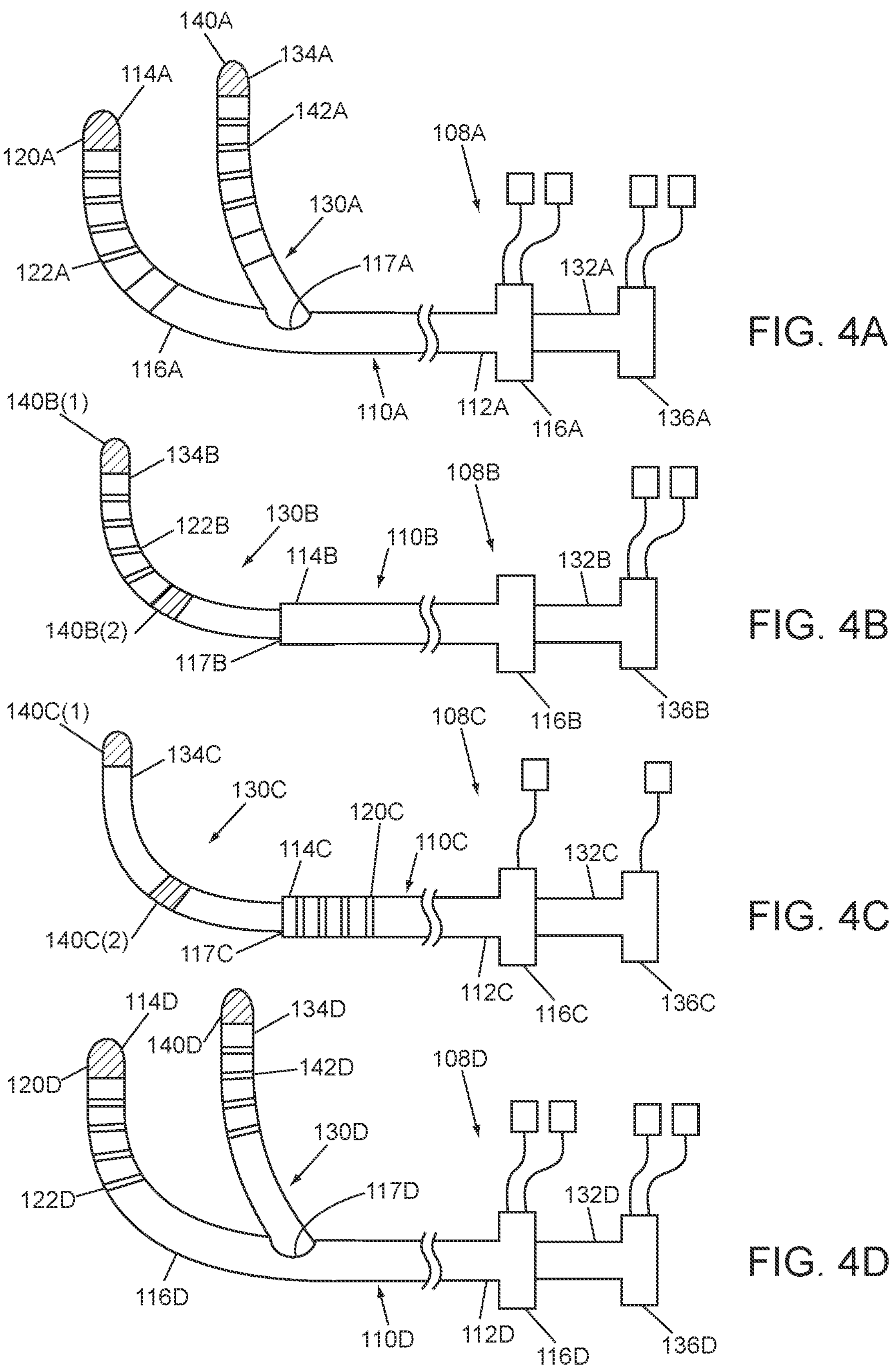
FIGS. 4A-4D are side views of alternative embodiments of catheter devices carrying a plurality of positional sensors.

Further, in the embodiments shown in FIGS. 4A and 4D, the main catheter body 110A/110D includes a side port 117A/117D on the distal portion 116A/116D through which the distal end 134A/134D of the secondary catheter body 130A/130D may extend. Thus, the secondary catheter body 130A/130D may extend laterally from the main catheter body 110A/110D, which may facilitate advancing the distal end 134A/134D into a tributary vein when the distal portion 116A/116D is introduced into a coronary vein.

In the embodiments shown in FIGS. 4B and 4C, the secondary catheter body 130B/130C may extend from an opening 117B/117C in the distal end 114B/114C of the main catheter body 110B/110C such that the bodies telescope relative to one another along a common longitudinal axis. Optionally, a distal portion of any of the secondary catheter bodies 130 may include a pre-shaped distal segment, e.g., biased to a predetermined curved or curvilinear shape, which may facilitate advancing the distal end 134 from the main catheter body 110 into a tributary vein.

One or both of the outer and inner catheter bodies 110, 130 may include one or more sensors or antennae 120, 140 that may provide signals, which may be analyzed by a processor to identify a location and/or orientation of the sensors 120, 140 relative to the external reference frame of a generated electromagnetic field, e.g., to provide an internal reference frame, similar to previous embodiments. For example, as shown in FIGS. 4A and 4D, both bodies 110A/110D, 130A/130D include sensors 120A/120D, 140A/140D on their distal ends 114A/114D,134A/134D, while in FIGS. 4B and 4C, only the secondary catheter body 130B/130C includes sensors 120B(1)/120C(1), 120B(2)/120C(2) on its distal portion.

Optionally, one or both of the main and secondary catheter bodies 110, 130 may include one or more electrodes, e.g. electrodes 122, 142 configured for recording electrograms, measuring impedance, and/or providing other signals that may be processed or analyzed by the processor. Optionally, one or more of these additional electrodes may be coupled to a power or energy source (not shown) such that the electrode(s) may be activated to deliver energy to the patient's heart, e.g., for pacing, ablation, and the like.

With reference to FIGS. 4A and 4D, the distal portion 116A/116D of the main catheter body 110A/110D may be introduced into the patient's body (with the secondary catheter body 130A/130D retracted into the main catheter body 110A/110D), and positioned at a desired location, whereupon the distal end 134A/134D of the secondary catheter body 130A/130D may be advanced from the side port 117A/117D away from the longitudinal axis of the main catheter body 110A/110D, e.g., into a coronary venous tributary. In this manner, the relative location of the sensors 120A/120D, 140A/140D may be adjusted relative to one another to maximize their spacing and/or position them within desired veins and/or relative to desired anatomy.

The sensors 120A/120D, 140A/140D may be positioned distally on the bodies 110A/110D, 130A/130D, respectively, such that the sensors may be both stably positioned in venous tributaries, e.g., such that the resulting internal reference frame remains substantially stable relative to the contacted anatomy. In an exemplary method, the main catheter body 110A, 110D may be positioned such that the sensor 120A/120D is placed in a great cardiac vein or anterior cardiac vein while the sensor 140A/140D is positioned in a lateral or postero-lateral cardiac vein (not shown).

Optionally, in addition to the positional antennae or sensors described above, in any of the embodiments herein, one or more external sensors (not shown) may be placed on the patient, e.g., on the patient's thorax, e.g., to track respiratory cycle, and/or on the patient spine, e.g., as a fixed skeletal reference. Information from such sensors may be integrated with information from the positional sensors to improve the ability to generate a stable internal reference frame relative to the anatomy. Further, e.g., with a sensor placed on the thorax, periodic changes in anatomical position, e.g., from the patient's respiratory cycle, may be tracked and used to generate a positional offset for an electro-anatomical map.

Further optionally, in any of the embodiments herein, the relative position between two or more positional sensors may be used to track periodic heart expansion/contraction, e.g., due to cardiac cycle, non-periodic heart expansion/contraction, e.g., due to patient volume status and/or other changes in the patient's anatomy. For example, if the patient's volume status increases, e.g., leading to an increase in the cardiac size, the distance between positional sensors may change this information, and the change in location and/or distance may be analyzed by the processor to maintain or re-establish an accurate relationship between the anatomy and the external reference frame.

As described above, the relationship between the anatomy and the external reference frame may change with patient movement or due to physiologic factors. It may then be necessary or desirable to compensate for this change in order to maintain an accurate relationship of a previously created detailed anatomical map to the externally generated reference. This compensation may occur at discrete points in time, e.g., after observed patient movement or after cardioversion, which typically induces significant patient movement, or it may occur at pre-defined intervals, or relatively continuously. In the case where the such compensation is made frequently, significant computational power may be required to update and render a detailed anatomical map. In this case, it may be beneficial to perform such computations using a GPU to manipulate one or more matrices representing the positional information comprising the anatomical map.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for facilitating imaging a patient during a medical procedure, comprising:

an electromagnetic field generator for generating an electromagnetic field around a desired region of a patient's body to provide an external reference frame;

a first elongate member comprising a proximal end, a distal end sized for introduction into the patient's body, and a first distal portion carrying a first positional sensor;

a second elongate member comprising a second distal portion advanceable from the first distal portion and carrying a second positional sensor such that a location of the second positional sensor is adjustable relative to the first positional sensor; and a processor coupled to the first and second positional sensors for receiving signals from the first and second positional sensors generated in response to the electromagnetic field, the processor configured to identify when the first and second positional sensors move relative to the external reference frame to identify corresponding movement of the patient's body.

2. The system of claim 1, further comprising a display coupled to the processor for presenting an anatomical map of at least a portion of the patient's body, the processor configured to reorient the anatomical map based at least in part on the identified movement of the patient's body to compensate for the movement.

3. The system of claim 1, further comprising a display coupled to the processor for presenting images of at least a portion of the patient's body, the processor configured to modify images presented on the display based at least in part on the identified movement of the patient's body to compensate for the movement.

4. The system of claim 1, wherein the first positional sensor is configured to provide first signals to the processor corresponding to positional and rotational coordinates of the first positional sensor relative to the external reference frame, and the second positional sensor is configured to provide second signals to the processor corresponding to positional coordinates of the second positional sensor relative to the external reference frame, and wherein the processor analyzes the first and second signals to generate an internal reference frame corresponding to an orientation of the patient's body within the external reference frame.

5. The system of claim 4, wherein the processor is configured to generate the internal reference frame as a three-dimensional internal reference frame from the first and second signals.

6. The system of claim 4, wherein the distal portion is configured for introduction into an organ of the patient's body, and wherein the processor is configured to analyze the first and second signals to generate the internal reference frame to identify an orientation of the organ within the external reference frame.

7. The system of claim 1, wherein the processor is configured to analyze the signals to generate an internal reference frame corresponding to an orientation of the patient's body within the external reference frame.

8. The system of claim 7, wherein, after generating the internal reference frame, the processor is configured to map the internal reference frame to the external reference frame such that, when the signals from the first and second positional sensors indicate the patient's body has moved, the internal reference frame may be remapped to the external reference frame.

9. The system of claim 1, wherein the second distal portion is advanceable laterally from the first distal portion.

10. The system of claim 9, wherein the second elongate member is advanceable from a side port in the first distal portion such that the second distal portion is directable laterally relative to the first distal portion.

11. The system of claim 9, wherein the second elongate member is advanceable axially from an end port in the first distal portion such that a distance between the first and second sensors is adjustable.

12. The system of claim 1, wherein the first and second distal portions are movable independently relative to the distal end such that a distance between the first positional sensor and the second positional sensor is adjustable.

13. A system for facilitating imaging of a patient's heart during a medical procedure, comprising:

an electromagnetic field generator for generating an electromagnetic field around a desired region of a patient's body to provide an external reference frame;

an elongate member comprising a proximal end, a distal end sized for introduction into the patient's body, and a distal portion carrying a plurality of sensors spaced apart from one another such that the sensors may be positioned within a coronary vessel; and a processor coupled to the sensors for receiving signals from the sensors to generate an internal reference frame substantially fixed relative to the coronary vessels to identify an orientation of the patient's heart within the external reference frame, the processor further configured to identify when the plurality of sensors move relative to the external reference frame to identify corresponding movement of the patient's body, wherein the plurality of sensors comprises a first positional sensor and a second positional sensor movable relative to the first position sensor such that a location of the second positional sensor is adjustable relative to the first positional sensor.

14. The system of claim 13, wherein, after generating the internal reference frame, the processor is configured to map the internal reference frame to the external reference frame such that, when the signals from the sensors indicate the patient's body has moved, the internal reference frame is remapped to the external reference frame based at least in part on the movement of the patient's body.

15. The system of claim 13, further comprising a display coupled to the processor for presenting an anatomical map of at least a portion of the patient's heart, the processor configured to reorient the anatomical map based at least in part on the identified movement of the patient's heart to compensate for the movement.

16. The system of claim 13, further comprising a display coupled to the processor for presenting images of at least a portion of the patient's heart, the processor configured to modify images presented on the display based at least in part on the identified movement of the patient's heart to compensate for the movement.

17. The system of claim 13, wherein the first positional sensor is configured to provide first signals to the processor corresponding to positional and rotational coordinates of the first positional sensor relative to the external reference frame, and the second positional sensor is configured to provide second signals to the processor corresponding to positional coordinates of the second positional sensor relative to the external reference frame, and wherein the processor is configured to analyze the first and second signals to generate a three-dimensional internal reference frame corresponding to an orientation of the patient's heart within the external reference frame.

18. A method for maintaining a stable spatial reference frame relative to cardiac anatomy within a patient's heart, comprising:

introducing a distal portion of an elongate member into the patient's heart such that a first sensor carried on the distal portion is positioned within a coronary sinus;

advancing a second sensor relative to the first sensor such that the second sensor is positioned within a tributary vein to adjust a distance between the first sensor and the second sensor;

generating an electromagnetic field that encompasses the patient's heart to provide an external reference frame;

receiving signals from the first and second sensors to identify locations of the first and second sensors relative to the external reference frame;

identifying when the locations of the first and second sensors move relative to the external reference frame to identify movement of the patient's heart; and compensating for movement of the patient's heart in images presented on a display.

19. The method of claim 18, wherein introducing the distal portion comprises positioning the first sensor within the coronary sinus and advancing a secondary body carrying the second sensor from the distal portion into the tributary vein.

20. The method of claim 19, wherein the secondary body is advanced laterally from the distal portion into the tributary vein.

* * * * *